(12) United States Patent
Aliyev et al.

(10) Patent No.: US 8,524,845 B2
(45) Date of Patent: Sep. 3, 2013

(54) CATALYST COMPOSITION AND A PROCESS FOR THE OLIGOMERIZATION OF ETHYLENE

(75) Inventors: Vugar O. Aliyev, Riyadh (SA); Atieh Abu-Raqabah, Riyadh (SA); Fahad Al-Khodairi, Riyadh (SA); Akif H. Azizov, Baku (AZ); Akber A. Khanmetov, Baku (AZ); Bilal V. Guliyev, Baku (AZ); Reyhan V. Aliyeva, Baku (AZ); Chingiz K. Rasulov, Baku (AZ); Minavar J. Ibrahimova, Baku (AZ)

(73) Assignee: Saudi Basic Industries Corporation, Riyadh (SA)

( * ) Notice: Subject to any disclaimer, the term of this patent is extended or adjusted under 35 U.S.C. 154(b) by 936 days.

(21) Appl. No.: 12/223,218

(22) PCT Filed: Feb. 6, 2007

(86) PCT No.: PCT/EA2007/000001
§ 371 (c)(1),
(2), (4) Date: Oct. 19, 2009

(87) PCT Pub. No.: WO2007/090412
PCT Pub. Date: Aug. 16, 2007

(65) Prior Publication Data
US 2010/0152398 A1 Jun. 17, 2010

(30) Foreign Application Priority Data
Feb. 8, 2006 (EP) ..................................... 06002513

(51) Int. Cl.
*C08F 4/64* (2006.01)
*C08F 4/76* (2006.01)
*C08F 4/52* (2006.01)

(52) U.S. Cl.
USPC ............ 526/161; 526/160; 526/170; 526/352

(58) Field of Classification Search
USPC .................................................. 526/172, 161
See application file for complete search history.

(56) References Cited

U.S. PATENT DOCUMENTS

| | | | | |
|---|---|---|---|---|
| 4,032,590 | A * | 6/1977 | Burnham | 585/18 |
| 4,361,714 | A | 11/1982 | Langer et al. | |
| 4,377,720 | A | 3/1983 | Langer | |
| 4,396,788 | A | 8/1983 | Langer, Jr. | |
| 4,409,409 | A | 10/1983 | Langer, Jr. et al. | |
| 4,410,750 | A | 10/1983 | Langer, Jr. | |
| 4,434,312 | A | 2/1984 | Langer, Jr. | |
| 4,434,313 | A | 2/1984 | Langer, Jr. | |
| 4,442,309 | A | 4/1984 | Langer, Jr. | |
| 4,486,615 | A | 12/1984 | Langer, Jr. | |
| 4,783,571 | A | 11/1988 | Chang et al. | |
| 4,783,573 | A | 11/1988 | Shiraki et al. | |
| 5,345,023 | A | 9/1994 | Chauvin et al. | |
| 6,555,633 | B1 * | 4/2003 | Tanaka et al. | 526/160 |
| 6,787,499 | B2 * | 9/2004 | Tanaka et al. | 502/152 |
| 2004/0068066 | A1 | 4/2004 | Blom et al. | |

FOREIGN PATENT DOCUMENTS

| | | |
|---|---|---|
| EP | 0241596 A1 | 10/1987 |
| EP | 0435367 A1 | 7/1991 |
| EP | 0 606 125 A | 7/1994 |
| EP | 606 125 A2 * | 7/1994 |
| JP | 2000302812 A | 10/2000 |
| WO | WO/80/00224 | 2/1980 |
| WO | WO 2004/052980 A1 * | 6/2004 |

OTHER PUBLICATIONS

Lian et al., Angew. Chem. Int. End. 2007,46, 8507-8510.*
Corazza et al., Inorg. Chem. 1991, 30, 145-148.*
Matsuo et al., J. Am. Chem. Soc. 2006, 128, 12362-12363.*
Chisolm et al., Polyhedron, 1997, 16, 2941-2949.*
Lian, B.; Beckerle, K.; Spaniol, T.P.; Okuda, J. Angew. Chem. Int. Ed. 2007, 46, 8507-8510.*
Japanese Patent No. 2000302812 (A); Publication Date: Oct. 31, 2000, Abstract Only; 1 Page.
International Publication No. 8000224 (A1); Publication Date: Feb. 21, 1980; Abstract Only; 1 Page.
Novelty Search Report; State Intellectual Property Office of the P.R. China; Application No. GCC/P/2007/7546; Filing Date: Jan. 6, 2007; 11 Pages.
International Preliminary Report on Patentability; International Application No. PCT/EA2007/000001; International Filing Date: Feb. 6, 2007; Date of Mailing: Sep. 7, 2007; 20 Pages.
International Search Report; International Application No. PCT/EA2007/000001; International Filing Date: Feb. 6, 2007; Date of Mailing: Sep. 7, 2007; 7 Pages.
Written Opinion of the International Searching Authority; International Application No. PCT/EA2007/000001; International Filing Date: Feb. 6, 2007; Date of Mailing: Sep. 7, 2007; 9 Pages.
Zhu et al: "Preparation & Structures . . . " J. Organometallic Chem, Elsevier-Sequoia S.A. Lausanne, CH, v 690, No. 17, (Sep. 1, 2005) p. 3929-3936.
Okuda J et al: "Syndiospecific Polymerization . . . " Macromolecular Chemistry and Physics, Wiley-VCH Verlag, Weinheim, DE, vol. 199, 1998, p. 543-545.
Linden Van Der A et al: "Polymerization of A-Olefins and Butadine . . . " J of the Amer Chem Society, Amer Chem Society, Washington, D.C., US, v 117, No. 11, 1995, p. 3008-3021.
Fokken S. et al: "Nine-Membered Titanactyclic . . . " Organometallics, Washington, DC, US, v 16, No. 20, 1997, p. 4240-4242.
Sernetz F G et al: "Copolymerization of Ethene . . . " Macromolecules, ACS, Washington, DC, US, vol. 30, No. 6, (Mar. 24, 1997), p. 1562-1569.
Froese, Robert D. J. et al Froese, Robert D.J. et al: "Theoretical Studies of Ethylene . . . "J of the Amer Chem Society, 119(31), 7109-7196 Coden.

* cited by examiner

*Primary Examiner* — Rip A. Lee
(74) *Attorney, Agent, or Firm* — Cantor Colburn LLP

(57) ABSTRACT

The present invention relates to a catalyst composition for the oligomerization of ethylene comprising at least one transition metal bisphenolate compound and at least one cocatalyst. The transition metal bisphenolate is a zirconium bisphenolate.
The invention also relates to a process for the oligomerization of ethylene in the presence of the catalyst composition according to the invention. The process results in a high yield of $C_4$-$C_{18}$ linear alpha-olefin and $C_6$-$C_{10}$ linear alpha-olefin.

8 Claims, No Drawings

CATALYST COMPOSITION AND A PROCESS FOR THE OLIGOMERIZATION OF ETHYLENE

CROSS REFERENCE TO RELATED APPLICATIONS

This application is a 371 of International Application No. PCT/EA2007/000001, filed Feb. 6, 2007, which claims priority to European Application No. 06002513.7, filed Feb. 8, 2006, both of which are hereby incorporated by reference in their entirety.

The invention relates to a process for the oligomerization of ethylene in the presence of a catalyst composition comprising at least one transition metal bisphenolate compound and at least one cocatalyst.

Linear Alpha Olefins (LAO) are olefins with a chemical formula $C_xH_{2x}$, distinguished from other mono-olefins with a similar molecular formula by linearity of the hydrocarbon chain and the position of the double bond at the primary or alpha position. Linear alpha olefins are a range of industrially important alpha-olefins, including 1-butene, 1-hexene, 1-octene, 1-decene, 1-dodecene, 1-tetradecene, 1-hexadecene, 1-octadecene and higher blends of $C_{20}$-$C_{24}$, $C_{24}$-$C_{30}$, and $C_{20}$-$C_{30}$ ranges.

There is a wide range of applications for linear alpha olefins. The olefins with lower carbon numbers for example 1-butene, 1-hexene and 1-octene are overwhelmingly used as co monomers in production of polyethylene. Another significant use of $C_4$-$C_8$ linear alpha olefins is for production of linear aldehyde The predominant application of 1-decene is in making polyalphaolefin synthetic lubricant base stock and to make, in a blend with higher linear alpha olefins, surfactants. $C_{10}$-$C_{14}$ linear alpha olefins are used in making surfactants for aqueous detergent formulations. These carbon numbers may be reacted with benzene to make linear alkyl benzene which is further sulfonated to linear alkyl benzene sulfonate. Although some $C_{14}$ alpha olefin is sold into aqueous detergent applications, $C_{14}$ has other applications such as being converted into chloroparaffins and as on-land drilling fluid base stock, $C_{16}$-$C_{18}$ linear olefins find their primary application as the hydrophobic part in oil-soluble surfactants and as lubricating fluids themselves. $C_{16}$-$C_{18}$ alpha or internal olefins are used as synthetic drilling fluid base for high value, primarily off-shore synthetic drilling fluids and in paper sizing. $C_{20}$-$C_{30}$ linear alpha olefins are used in a number of reactive and non-reactive applications, including as feedstock to make heavy linear alkyl benzene and low molecular weight polymers which are used to enhance properties of waxes.

Linear alpha-olefins are usually prepared by the catalytic oligomerization of ethylene in the presence of a Ziegler-Natta-type catalyst. Important requirements of the ethylene oligomerization are the desired selectivity and the desired product distribution. The applied catalyst and the process conditions are essential features to obtain these desired characteristics.

Various types of catalysts are known to be applied in the process for the oligomerization of ethylene.

An example of a known catalyst system includes a binary catalyst system comprising an ethyl aluminum chloride combined with titanium tetrachloride, optionally with further admixture of a third component, such as for example an electron donor, to enhance the selectivity. Another known catalyst system includes a binary catalyst comprising an ethyl aluminum chloride combined with a zirconium containing compound.

However, these catalyst compositions are not quite satisfactory in respect of activity and selectivity. The use of zirconium-containing catalysts is disclosed in for example U.S. Pat. Nos. 4,486,615; 4,442,309; 4,434,313; 4,434,312; 4,410,750; 4,409,409; 4,396,788; 4,377,720 and 4,361,714. The oligomerization of ethylene using these catalysts is performed in hydrocarbon solvents at a temperature between 100° C. and 150° C. and at elevated pressures between 0.4 MPa and 0.8 MPa. The main disadvantages of said catalysts are the poor solubility of zirconium tetrachloride in hydrocarbon solvents, the severe conditions for operation of the catalyst and its relatively low selectivity. During the oligomerization of ethylene, significant amounts of undesirable wax and polymer are formed under the influence of these catalysts.

U.S. Pat. No. 4,783,573 discloses the use of a ternary catalyst system comprising a zirconium halide, an organoaluminum compound and a Lewis base, and adding a catalyst deactivating agent to the resulting reaction mixture. The disadvantage of this process is the relatively low selectivity of $C_6$-$C_{10}$ fraction (30-56%) in combination with the high yield of $C_{20+}$ fraction. U.S. Pat. No. 5,345,023 discloses a process for oligomerization of ethylene to light alpha-olefins, mainly 1-butene, 1-hexene, 1-octene and 1-decene using a catalyst obtained by mixing a zirconium compound with an organic compound chosen from the class of acetals and ketals and with a chorine or bromine-containing compound of aluminum hydrocarbyl. This system exhibits low selectivity (33-57 wt %) for $C_6$-$C_{10}$ fraction.

WO1980/00224 discloses a catalyst comprising a zirconium carboxylate and an organ aluminum compound. The main disadvantages of that catalyst system are the low selectivity of $C_6$-$C_{10}$ fraction and the formation of undesired by-products such as oligomers of $C_{20+}$ wax and polyethylene. The formation of heavy oligomers which are waxy solids and only partly soluble in the product mix of linear alpha-olefins causes reactor plugging and consequently frequent reactor shut downs for cleaning.

Ethylene may be oligomerized into linear alpha-olefins efficiently using metal-complex catalysts on the basis of titanium and zirconium compounds. However, the known catalysts are either non-technological or not highly-selective for the production of the most valuable and desirable narrow fractions of alpha-olefins, for example the $C_4$-$C_{10}$ fraction and the $C_6$-$C_{10}$ fraction.

It is an object of the present invention to provide a catalyst composition having an improved activity and an improved selectivity for the preparation of linear low molecular weight alpha olefins preferably with an improved $C_6$-$C_{10}$ fraction yield.

The process according to the present invention is characterised in that the oligomerization temperature ranges between 30° C. to about 120° C. and ethylene is contacted in a reactor with a catalyst composition comprising at least one transition metal bisphenolate compound and at least one co catalyst where the transition metal bisphenolate is a zirconium (IV) bisphenolate represented by formula (I):

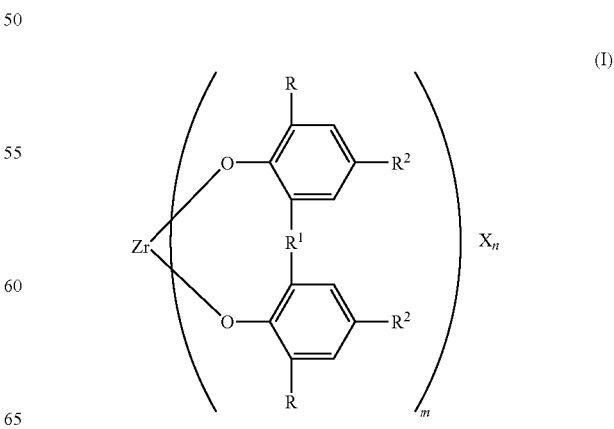

wherein
R and R² may be, independently of one another, the same or different, H, alkyl, aryl, cycloalkyl or halogen;
R¹ is selected from —CH₂—, —CHR— wherein R is selected from H, (C₁-C₂₀) alkyl, (C₆-C₂₀) aryl, (C₃-C₁₀) cycloalkyl and halogen and (—CH₂—)₂;
X is selected from halogen, β-diketonate, —OR and —OOCR wherein R may be H, alkyl, aryl, cycloalkyl or halogen
m=1 or 2 and
n=0 or 2.

Preferably, the oligomerization temperature ranges between 50° C. to 100°.

The process according to the present invention results in a selectively oligomerization of ethylene to linear alpha-olefins having a high yield of $C_4$ to $C_{18}$ fraction. According to a preferred embodiment of the invention R=H, $(C_1-C_{20})$alkyl, $(C_6-C_{20})$aryl, $(C_3-C_{10})$cycloalkyl or halogen.

According to a further preferred embodiment of the invention R is $C(CH_3)_3$—, methylcyclohexyl or phenyl.

The essential bridging groups R¹ in the zirconium (IV) bisphenolate according to formula (I) are —CH₂—, —CHR—, and (—CH₂—)₂.

According to a preferred embodiment of the invention R¹ is selected from —CH₂—, —CHR— and (—CH₂—)₂.

Preferably in —CHR— R=H, $(C_1-C_{20})$alkyl, $(C_6-C_{20})$aryl, $(C_3-C_{10})$cycloalkyl or halogen.

According to a further preferred embodiment of the invention R¹ is selected from —CH₂—, —CH(CH₃)— and (—CH₂—)₂.

According to a more preferred embodiment of the invention R¹ is —CH₂—.

According to a preferred embodiment of the invention R²=H, $(C_1-C_{20})$alkyl, $(C_6-C_{20})$aryl, $(C_3-C_{10})$cycloalkyl or halogen.

According to a further preferred embodiment R²=H, $(C_1-C_{20})$alkyl, $(C_3-C_{10})$cycloalkyl or halogen.

According to a more preferred embodiment R²=H, $CH_3$ or $C(CH_3)_3$.

The preferred halogen in R, R² and X is chlorine.

Additional substituents other than R and R² may be also provided at the aromatic rings of the bisphenolate system, i.e. at other carbon atoms of the aromatic rings.

According to a preferred embodiment of the invention X is selected from chlorine, β-diketonate, —OR and —OOCR wherein R=H, $(C_1-C_{20})$alkyl, $(C_6-C_{20})$aryl, $(C_3-C_{10})$cycloalkyl or halogen.

According to a preferred embodiment of the invention the zirconium bisphenolate is 2,2'-bissubstituted zirconium(IV) cresolate and/or zirconium(IV) methylene bisphenolate.

A preferred co catalyst is an organo aluminium compound.

Preferably, the organo aluminium compound is represented by the formula $R^3_pAlY_{3-p}$,
wherein
$R^3=(C_1-C_{20})$alkyl
Y=halogen and
$1 \leq p \leq 2$.
More preferably Y=chlorine.
More preferably $1.5 \leq p \leq 2$.

According to another preferred embodiment of the invention the organo aluminium compound is diethyl aluminium chloride and/or ethyl aluminium sesquichloride.

Preferably the molar ratio of co catalyst to transition metal ranges between about 10:1 to about 100:1. More preferably the molar ratio ranges between about 15:1 to about 70:1 and even more preferably the molar ratio ranges between about 20:1 to about 50:1.

The catalyst composition may comprise at least one electron donor compound. Examples of suitable electron donor compounds include ethyl acetate, ethyl acetoacetate, ethyl benzoate, anisol, thiophene, tetrahydrofuran, cyclopentylamine and 2-pyrrolidone. Generally the molar ratio electron donor compound: Zr compound ranges between 1:0.1 and 1:3.

According to a preferred embodiment of the invention the co catalyst is added to the reactor in a first step to obtain the desired high activity and selectivity of the catalyst composition.

The invention also relates to a process for the oligomerization of ethylene wherein ethylene is contacted in a reactor with the catalyst composition according to the present invention.

Preferably, the oligomerization temperature ranges between about 30° C. to about 120° C.

More preferably the oligomerization temperature ranges between about 50° C. to about 100° C.

Preferably the ethylene pressure ranges between about 1 MPa to about 5 MPa. More preferably the ethylene pressure ranges between about 2 MPa to about 4 MPa.

A very important advantage of the catalyst composition according to the present invention is that the use of this catalyst results in a selectively oligomerization of ethylene to linear alpha-olefins having a high yield of $C_6$ to $C_{10}$ fraction.

It is a further advantage of the present invention that the formation of high molecular weight polymer is minimized or even eliminated at all.

Another advantage of the present invention is that the catalyst composition and the conditions under which the ethylene oligomerization process is carried out result in a Poisson type distribution of the oligomerization product distribution whereas a Schultz-Flory type distribution is characteristic for the known zirconium-containing catalytic systems. The advantage of the Poisson type distribution is that this distribution provides an increased yield of $C_6$ to $C_{10}$ and other middle α-olefin fractions. In general the existing Zr-containing catalysts are characterized by Schultz-Flory type distribution which results in a wide range of ethylene oligomerization products with less $C_6$ to $C_{10}$ fraction yield.

Preferably, the catalyst composition according to the present invention is prepared by dissolving the components in aromatic, halide aromatic and/or aliphatic solvents. For preparing the catalyst composition, there is no particular limitation on the order of addition of the catalyst components required. Preferably the catalyst system used in the production of linear alpha-olefins is dissolved in an inert organic solvent.

Examples of suitable organic solvents include aromatic hydrocarbon solvents which may be unsubstituted or substituted with halogens for example toluene, benzene, xylene, monochlorobenzene, dichlorobenzene, chlorotoluene, aliphatic paraffin hydrocarbons for example pentane, hexane, heptane, octane, nonane, decane, alicyclic hydrocarbon compounds for example cyclohexane, decahydronaphthalene, and halogenated alkanes for example dichloroethane and dichlorobutane.

It is further preferred to exclude oxygen, moisture and aggressive impurities from the reactants and the solvent.

An important aspect of the invention is the mode of reaction of ethylene with the catalyst composition dissolved in the inert solvent.

The catalyst components may be contacted at a temperature in the range between about –30° C. to 50° C. and may be kept in the absence of ethylene up to 24 hours prior to addition into the oligomerization reactor.

In a preferred embodiment of the invention the catalyst components are directly contacted in the oligomerization reactor with ethylene to obtain the high activity.

When the oligomerization reaction is conducted at pressures of ethylene about ≦1 MPa, the ethylene feed has to be supplied continuously to the reactor to minimize or prevent the deactivation of the oligomerization centers, the formation of polymer, internal and branched olefins and to reach high $C_6$-$C_{10}$ alpha-olefin selectivity. At pressures about ≧1MPa the oligomerization reaction may be conducted both at constant and at changeable pressures.

The main reason behind deactivation of the oligomerization centers is the bimolecular destruction of the intermediate metal-organic oligomerization centers. This deactivation process leads to the decrease in oligomerization activity. In some cases as a result of the intermediate metal-organic centers destruction the transition metal passes to its less oxidation state favorable for the polymerization activity of the catalyst. The presence of bulky bisphenolate ligands in the coordination sphere strongly restricts the bimolecular deactivation of oligomerization centers. This, in turn, leads to the increase of their stability and the stability of the catalyst as a whole. The bulky bisphenolate ligands are favorable for the increase of metal-cationic character of the catalytic centers, responsible for oligomerization (dimerization) activity of the catalyst, due to more effective separation of positively charged transition metal-organic centers from negatively charged Al-containing complex counterion. As a result, the total effect arises with an increased oligomerization activity and decreased (or eliminated) polymerization activity in the course of ethylene oligomerization.

On the other hand the increased metal-cationic character of oligomerization centers intensifies the chain transfer processes going through the β-hydrogen elimination in these centers. Thus the catalytic centers become more prone to lead the dimerization and trimerization reaction of ethylene instead of its long chain oligomerization process. As a result, at the early stages the rapid accumulation of dimerization and trimerization products takes place. The accumulation of the first dimerization product, 1-butene, follows by its secondary codimerization with ethylene (hydrovinylation) yielding 1-hexene. The accumulation of 1-hexene follows by its codimerization with ethylene obtaining for example 1-octene. The codimerization (hydrovinylation) rate decreases rapidly in the line 1-butene>>1-hexene>1-octene>1-decene. Such a serial-parallel dimerization process leads to the deviation from Schultz-Flory distribution and, hence, to the increase in $C_6$-$C_{10}$ alpha-olefin content in the product. High selectivity in alpha-olefin content (>98-99%) is also provided by the presence of bulky bisphenolate ligands in inner coordination sphere of the transition metal, directing the transition metal atom to the end of the intermediate oligoalkyl-zirconium chain obtained as a result of alpha-olefin addition to intermediate zirconium-H species addition in the course of chain transfer reaction.

The $C_6$-$C_{10}$ linear alpha-olefin obtained with the process according to the invention is a colourless and transparent liquid. The structure of $C_6$-$C_{10}$ linear a-olefins has been determined by gas chromatography, infra-red- and NMR-spectral methods. This analysis shows that the alpha-olefin purity of the linear alpha-olefins according to the invention ranges between about 95% and 98%.

Zhu et al. disclose zirconium complexes in the publication "Preparation and structure of 6- and 7-coordinate salen-type zirconium complexes and their catalytic properties for oligomerization of ethylene" in the Journal of Organometallic Chemistry (17 Sep. 2005, pages 3929-3936). In contrast to the present invention the salen- and salphen type zirconium complexes described by Zhu et al have in their structure diimine type bridging groups (—CH═N CH2-CH2 N═CH—, —CH═N-Ph-N═CH). These 6- and 7-coordinated salen- and salphen type zirconium complexes have very rigid saturated octahedral (or more) coordination sphere. On that reason it is difficult to activate them by aluminum-organic compounds at temperatures below 100° C. A higher temperature is needed to make their coordination sphere more mobile (flexible) to be able to react with aluminum-organic activators. The precursors according to the present invention have 4- and 5-coordinated unsaturated and mobile coordination sphere. On that reason they easily react with aluminum organic compounds to give active centers mediating oligomerization process at lower temperatures. The catalytic systems according to Zhu are unstable and exhibit only moderate activity only at temperatures higher than 150° C. The systems according to the present invention are more stable and have high activity at temperatures between for example 50° C. and 100° C. Furthermore the olefin purity of oligomerization products obtained using the precursors according to Zhu is low (between 74.9% and 91.6%) which makes them unusable as co-monomers in ethylene polymerization processes.

The invention will be elucidated with reference to the following non-limiting examples.

EXAMPLES 1-20

In the examples the oligomerization of ethylene was carried out in the presence of the specified catalyst for a period of 0.5-2 hours.

The experimental conditions of the examples are summarised as follows:

All materials were handled in a nitrogen atmosphere using either schlenk techniques or nitrogen filled glove box. Nitrogen and toluene were purchased or supplied from a plant source and were dried through an additional bed of molecular sieves, if necessary.

The examples 1-18 and 19-20 were carried out in two different reactors.

The examples 1-18 were carried out in a reactor from stainless steel with a capacity of 0.5 liter. After consuming a certain volume of ethylene, an autoclave was disconnected from ethylene supplying line and cooled up to room or lower (up to −35° C.) temperature. The un-reacted part of ethylene and some quantity of the synthesized butene-1 were passed through a trap cooled by a mixture of dry ice with acetone.

Then 2 ml of aqueous NaOH solution (10%) was added into the autoclave and the reaction mixture was stirred within 5 minutes for deactivation of catalyst. The condensed butene-1 was analyzed by the GC method. The liquid products of reaction were discharged from the autoclave and analyzed by the method of gas-liquid chromatography.

The examples 19-20 were conducted in a 2-liter stainless steel reactor vessel, jacketed with external/internal cooling coils. Feeding the ethylene and nitrogen gases into the reactor were controlled by mass flow controllers. The mass flow controllers operated with the computer control system to control flow rate per minute and total gas flow.

After the reaction was continued for indicated amount of time with maintaining the reaction conditions, the reaction was stopped by adding 20 ml ethanol to the reaction mixture. The linear alpha-olefin product obtained was separated, collected and analyzed by gas chromatography.

The applied zirconium bisphenolate complexes and the results of the experiments are shown in Table 1.

EXAMPLE 1

A solution of zirconium bisphenolate complex 1 (0.2 mmoles, 0.116 g) in 50 ml of dry toluene was charged into a 200 ml autoclave cleared and dried in vacuum, supplied with a magnetic mixer.

Then a solution of diethylaluminiumchloride [DEAC] (6 mmoles, 0.723 g) in 10 ml of toluene was added. The molar ratio of the catalyst components was Al:Zr=30:1. The autoclave was connected to an ethylene line and heated until 70° C.

Then ethylene was introduced into the autoclave until a pressure of 3 MPa was reached and the ethylene oligomerization process was carried out at 70° C. and 3 MPa of ethylene pressure for 60 minutes.

The quantity of the obtained linear alpha olefins (LAO) was 56.7 g.

The activity of the catalyst was 3108 g/g Zr. h.

EXAMPLE 2

A solution of zirconium bisphenolate complex 2 (0.162 mmoles, 0.081 g) in 50 ml of dry toluene was charged to the 200 ml autoclave, prepared as in example 1, and a solution of DEAC (6.48 mmoles, 0.78 g) in 20 ml of toluene was added. The molar ratio of the catalyst components was Al:Zr=40:1. The ethylene oligomerization process was carried out at 100° C. The pressure was kept constant (4 MPa) for the whole duration of the reaction (1 hour).

The quantity of the obtained linear alpha olefins (LAO) was 80.3 g.

The activity of the catalyst was 5436 g/g Zr.h.

EXAMPLE 3

The solution of zirconium bisphenolate complex 3 (0.150 mmoles, 0.140 g) in 60 ml of dry toluene was charged to the autoclave, and then a solution of DEAC (3.02 mmoles, 0.364 g) in 20 ml of toluene was added. The molar ratio of the catalyst components was Al:Zr=20:1. The ethylene oligomerization process was carried out at 100° C. The pressure was being kept constant (3 MPa) for the whole duration of the reaction (1 hour).

The quantity of the obtained linear alpha olefins (LAO) was 94.5 g.

The activity of the catalyst was 6907 g/g Zr.h.

EXAMPLE 4

A solution of zirconium bisphenolate complex 4 (0.15 mmoles, 0.106 g) in 30 ml of dry toluene was charged to the autoclave, and then a solution of DEAC (7.5 mmoles, 0.9 g) in 20 ml of toluene was added. The molar ratio of components was Al:Zr=50:1. The ethylene oligomerization process was carried out at 80° C. The pressure was kept constant (3 MPa) for the whole duration of the reaction (1 hour).

The quantity of the obtained linear alpha olefins (LAO) was 86.8 g.

The activity of the catalyst was 6345 g/g Zr.h.

In the formula as illustrated in Table 1 $C_5H_7O_2$=acetylacetone

EXAMPLE 5

A solution of zirconium bisphenolate complex 5 (0.116 mmoles, 0.081 g) in 30 ml of dry toluene was charged to the autoclave, and then a solution of DEAC (3.48 mmoles, 0.42 g) in 20 ml of toluene was added. The molar ratio of catalyst components was Al:Zr=30:1. The ethylene oligomerization process was carried out at 70° C. The pressure was kept constant (5 MPa) for the whole duration of the reaction (1 hour).

The quantity of the obtained linear alpha olefins (LAO) was 80.5 g.

The activity of the catalyst was 7608 g/g Zr.h.

In the formula as illustrated in Table 1 DBM**=dibenzoylmethane.

EXAMPLE 6

A solution of zirconium bisphenolate complex 6 (0.195 mmoles, 0.1129 g) in 30 ml of dry toluene was charged to the autoclave, and then a solution of diethyl aluminium sesquichloride (3.9 mmoles, 0.965 g) in 30 ml of toluene was added there. The molar ratio of components was Al:Zr=20:1. The ethylene oligomerization process was carried out at 120° C. The pressure was kept constant (2.5 MPa) for the whole duration of the reaction (30 minutes).

The quantity of the obtained linear alpha olefins (LAO) was 49.3 g.

The activity of the catalyst was 5543 g/g Zr.h.

EXAMPLE 7

A solution of zirconium bisphenolate complex 7 (0.121 mmoles, 0.064 g) in 30 ml of dry chlorobenzene was charged to the autoclave and then a solution of DEAC (2.42 mmoles, 0.29 g) in 30 ml of chlorobenzene was added. The molar ratio of catalyst components was Al:Zr=20:1. The ethylene oligomerization process was carried out at 50° C. The pressure was kept constant (1 MPa) for the whole duration of the reaction (2 hours).

The quantity of the obtained linear alpha olefins (LAO) was 58.8 g.

The activity of the catalyst was 2672 g/g Zr.h.

EXAMPLE 8

A solution of zirconium bisphenolate complex 8 (0.160 mmoles, 0.095 g) in 50 ml of dry benzene was charged to the autoclave, and then a solution of DEAC (8 mmoles, 0.964 g) in 30 ml of benzene was added. The molar ratio of catalyst components was Al:Zr=50:1. The ethylene oligomerization process was carried out at 60° C. The pressure was kept constant (3 MPa) for the whole duration of the reaction (1 hour).

The quantity of the obtained linear alpha olefins (LAO) was 70.8 g.

The activity of the catalyst was 4852 g/g Zr.h.

EXAMPLE 9

A solution of zirconium bisphenolate complex 9 (0.180 mmoles, 0.104 g) in 30 ml of dry toluene was charged to the autoclave, and then a solution of DEAC (2.7 mmoles, 0.325 g) in 20 ml of toluene was added. The molar ratio of catalyst components was Al:Zr=15:1. The ethylene oligomerization process was carried out at 80° C. The pressure was kept constant (2.5 MPa) for the whole duration of the reaction (1 hour).

The quantity of the obtained linear alpha olefins (LAO) was 30.8 g.

The activity of the catalyst was 1877 g/g Zr.h.

EXAMPLE 10

A solution of zirconium bisphenolate complex 10 (0.120 mmoles, 0.116 g) in 30 ml of dry toluene was charged to the autoclave, and then a solution of DEAC (7.8 mmoles, 0.94 g) in 20 ml of toluene was added. The molar ratio of components was Al:Zr=65:1. The ethylene oligomerization process was carried out at 70° C. The pressure was kept constant (3 MPa) for the whole duration of the reaction (30 minutes).

The quantity of the obtained linear alpha olefins (LAO) was 40.6 g.

The activity of the catalyst was 4451 g/g Zr.h.

EXAMPLE 11

A solution of zirconium bisphenolate complex 11 (0.25 mmoles, 0.132 g) in 30 ml of dry toluene was charged to the autoclave, and then a solution of DEAC (5 mmoles, 0.6 g) in 20 ml of toluene was added. The molar ratio of catalyst components was Al:Zr=20:1. The ethylene oligomerization process was carried out at 60° C. The pressure was kept constant (3 MPa) for the whole duration of the reaction (30 minutes).

The quantity of the obtained linear alpha olefins (LAO) was 34.4 g.

The activity of the catalyst was 3017 g/g Zr.h.

EXAMPLE 12

A solution of zirconium bisphenolate complex 12 (0.2 mmoles, 0.126 g) in 30 ml of dry toluene was charged to the autoclave and then a solution of DEAC (6 mmoles, 0.723 g) in 20 ml of toluene was added. The molar ratio of components was Al:Zr=30:1. The ethylene oligomerization process was carried out at 70° C. The pressure was kept constant (3 MPa) for the whole duration of the reaction (1 hour).

The quantity of the obtained linear alpha olefins (LAOs) was 45.5 g.

The activity of the catalyst was 2494 g/g Zr.h.

EXAMPLE 13

A solution of zirconium bisphenolate complex 13 (0.17 mmoles, 0.1053 g) in 50 ml of dry toluene was charged to the autoclave, and then a solution of DEAC (5.1 mmoles, 0.614 g) in 30 ml of toluene was added. The molar ratio of catalyst components was Al:Zr=30:1. The ethylene oligomerization process was carried out at 50° C. The pressure was kept constant (4 MPa) for the whole duration of the reaction (1 hour).

The quantity of the obtained linear alpha olefins (LAO) was 58 g.

The activity of the catalyst was 3742 g/g Zr.h.

EXAMPLE 14

A solution of zirconium bisphenolate complex 14 (0.165 mmoles, 0.0987 g) in 50 ml of dry toluene was charged to the autoclave, and then a solution of DEAC (6.6 mmoles, 0.795 g) in 20 ml of toluene was added. The molar ratio of catalyst components was Al:Zr=40:1. The ethylene oligomerization process was carried out at 80° C. The pressure was kept constant (4 MPa) for the whole duration of the reaction (1 hour).

The quantity of the obtained linear alpha olefins (LAO) was 65.8 g.

The activity of the catalyst was 4375 g/g Zr.h.

EXAMPLE 15

A solution of zirconium bisphenolate complex 15 (0.175 mmoles, 0.0896 g) in 30 ml of dry toluene was charged to the autoclave, and then a solution of DEAC (3.5 mmoles, 0.42 g) in 30 ml of toluene was added. The molar ratio of catalyst components was Al:Zr=20:1. The ethylene oligomerization process was carried out at 70° C. The pressure was kept constant (3 MPa) for the whole duration of the reaction (1 hour).

The quantity of the obtained linear alpha olefins (LAO) was 78.7 g.

The activity of the catalyst was 4931 g/g Zr.h.

EXAMPLE 16

A solution of zirconium bisphenolate complex 16 (0.19 mmoles, 0.103 g) in 50 ml of dry toluene was charged to the autoclave, and then a solution of DEAC (5.7 mmoles, 0.687 g) in 30 ml of toluene was added. The molar ratio of catalyst components was Al:Zr=30:1. The ethylene oligomerization process was carried out at 70° C. The pressure was kept constant (4 MPa) for the whole duration of the reaction (1 hour).

The quantity of the obtained linear alpha olefins (LAO) was 83.6 g.

The activity of the catalyst was 4824 g/g Zr.h.

EXAMPLE 17

A solution of zirconium bisphenolate complex 17 (0.2 mmoles, 0.1028 g) in 50 ml of dry toluene was charged to the autoclave, and then a solution of DEAC (6 mmoles, 0.723 g) in 20 ml of toluene was added. The molar ratio of catalyst components was Al:Zr=30:1. The ethylene oligomerization process was carried out at 70° C. The pressure was kept constant (3 MPa) for the whole duration of the reaction (1 hour).

The quantity of the obtained linear alpha olefins (LAO) was 77.8 g.

The activity of the catalyst was 4265 g/g Zr.h.

EXAMPLE 18

A solution of zirconium bisphenolate complex 18 (0.185 mmoles, 0.1038 g) in 40 ml of dry toluene was charged to the autoclave, and then a solution of DEAC (5.55 mmoles, 0.669 g) in 40 ml of toluene was added. The molar ratio of catalyst components was Al:Zr=30:1. The ethylene oligomerization process was carried out at 70° C. The pressure was kept constant (4 MPa) for the whole duration of the reaction (1 hour).

The quantity of the obtained linear alpha olefins (LAO) was 80.3 g.

The activity of the catalyst was 4759 g/g Zr.h.

EXAMPLE 19

200 ml Tolulene, 2.20 mmol ethyl aluminum sesquichloride (EASC) and 2.23 mmol DEAC were mixed in a 250 ml round bottom flask. Then 0.15 mmol of a zirconium bisphenolate complex 1 was added to the mixture. The molar ratio of Al/Zr was 29.5. The reaction was conducted at 70° C. and 2.5 MPa ethylene pressure. The oligomerization time was 60 minutes. 171 g of LAO was obtained.

The yield of LAO was 12500 g LAO/g Zr.

EXAMPLE 20

200 ml Tolulene, 0.25 mmol of a zirconium bisphenolate complex 1 and neat EASC (Al/Zr=35) were mixed in a 250 ml round bottom flask. The reaction was conducted at 80° C. and 3 MPa ethylene pressure. The oligomerization time was 60 minutes.

212 g of LAO was obtained.

The yield of LAO was 9298 g LAO/g Zr.

TABLE 1

| EXAMPLE | Formula of the zirconium-bisphenolate complex | Distribution of alpha-olefins (wt %) | | | |
|---|---|---|---|---|---|
| | | $C_4$ | $C_6$-$C_{10}$ | $C_{12}$-$C_{18}$ | $C_{20+}$ |
| 1 | 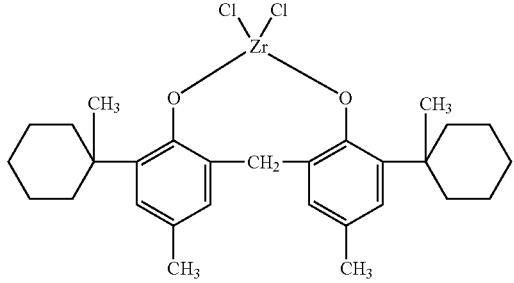 | 24.5 | 68.3 | 7 | 0.5 |
| 2 | 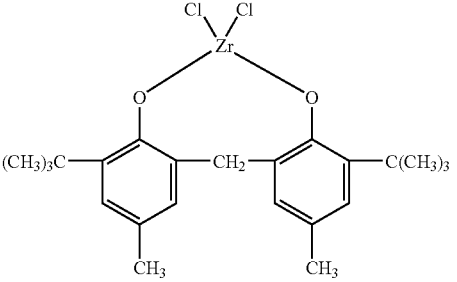 | 16.3 | 73.8 | 9.3 | 0.6 |
| 3 | 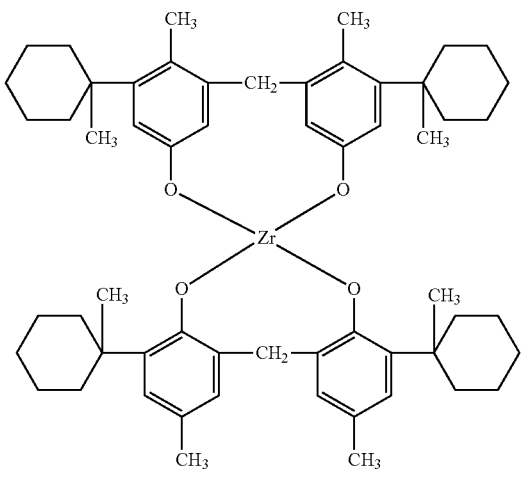 | 13.4 | 78.6 | 7.3 | 0.7 |

TABLE 1-continued

| EXAMPLE | Formula of the zirconium-bisphenolate complex | Distribution of alpha-olefins (wt %) | | | |
|---|---|---|---|---|---|
| | | $C_4$ | $C_6$-$C_{10}$ | $C_{12}$-$C_{18}$ | $C_{20+}$ |
| 4 | Zr(O$_2$H$_7$C$_5$)(C$_5$H$_7$O$_2$)* bridged bis(2-methylcyclohexyl-4-methylphenolate) | 19.3 | 76.4 | 4.1 | 0.2 |
| 5 | Zr(DBM)(DBM)** bridged bis(2-tert-butyl-4-methylphenolate) | 20.6 | 74.7 | 4.6 | 0.3 |
| 6 | ZrCl$_2$ bridged bis(2-methylcyclohexyl-4-methylphenolate) | 16.2 | 73.5 | 9.7 | 0.6 |
| 7 | ZrCl$_2$ bis(2-tert-butyl-4-methylphenolate) with CH(C$_2$H$_5$) bridge | 24.6 | 70.8 | 4.3 | 0.3 |
| 8 | ZrCl$_2$ bis(2-methylcyclohexyl-4-methylphenolate) with CH(CH$_3$) bridge | 25.8 | 65.7 | 8.3 | 0.2 |

TABLE 1-continued

| EXAMPLE | Formula of the zirconium-bisphenolate complex | Distribution of alpha-olefins (wt %) | | | |
|---|---|---|---|---|---|
| | | $C_4$ | $C_6$-$C_{10}$ | $C_{12}$-$C_{18}$ | $C_{20^+}$ |
| 9 | [structure] | 18.5 | 64.6 | 15.9 | 1.0 |
| 10 | [structure] | 38.3 | 53.7 | 7.5 | 0.5 |
| 11 | [structure] | 22.4 | 68.8 | 8.4 | 0.4 |
| 12 | [structure] | 5.6 | 41 | 33.4 | 20 |

TABLE 1-continued

| EXAMPLE | Formula of the zirconium-bisphenolate complex | Distribution of alpha-olefins (wt %) | | | |
|---|---|---|---|---|---|
| | | $C_4$ | $C_6$-$C_{10}$ | $C_{12}$-$C_{18}$ | $C_{20+}$ |
| 13 | [Zr complex with bisphenolate bridged by -CH2-NH-CH2-, aryl groups bearing CH3 and 1-methylcyclohexyl substituents] | 8.3 | 45.9 | 25.8 | 17.3 |
| 14 | [Zr complex with bisphenolate bridged by CH(CH3), aryl groups bearing tBu substituents] | 14.3 | 72.7 | 8.6 | 4.4 |
| 15 | [Zr complex with bisphenolate bridged by CH2, aryl groups bearing phenyl substituents] | 18.8 | 70.3 | 10.7 | 0.2 |
| 16 | [Zr complex with bisphenolate bridged by CH2, aryl groups bearing isopropyl, methyl, and Cl substituents] | 7.8 | 54.7 | 23.9 | 13.6 |
| 17 | [Zr complex with bisphenolate bridged by -CH2-CH2-, aryl groups bearing tBu and Me substituents] | 14.6 | 76.3 | 8.2 | 0.9 |

TABLE 1-continued

| EXAMPLE | Formula of the zirconium-bisphenolate complex | Distribution of alpha-olefins (wt %) | | | |
|---|---|---|---|---|---|
| | | $C_4$ | $C_6$-$C_{10}$ | $C_{12}$-$C_{18}$ | $C_{20^+}$ |
| 18 | [Zr complex with Pr-i-O, O-i-Pr, tBu, Me substituents] | 12.6 | 73.1 | 13.2 | 1.1 |
| 19 | [Zr complex with Cl, Cl, 1-methylcyclohexyl, CH₃ substituents] | 19.1 | 65.3 | 14.4 | 1.2 |
| 20 | [Zr complex with Cl, Cl, 1-methylcyclohexyl, CH₃ substituents] | 26.2 | 67.2 | 6.5 | 0.1 |

These examples and Table 1 show that the catalyst composition according to the present invention is advantageously applied in the oligomerization of ethylene. The catalyst results in a high yield of $C_6$-$C_{10}$ fraction and high activity of the catalyst.

The invention claimed is:

1. A process for the oligomerization of ethylene comprising contacting ethylene in a reactor with a catalyst composition comprising a transition metal bisphenolate compound and a co-catalyst wherein the transition metal bisphenolate is a zirconium (IV) bisphenolate represented by formula (I):

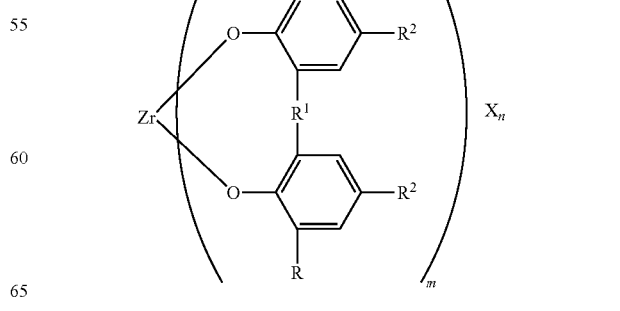

wherein

R and $R^2$ are, independently of one another, the same or different, H, alkyl, aryl, cycloalkyl or halogen;

$R^1$ is —$CH_2$—;

X is halogen, β-diketonate, —OR, or —OOCR, wherein R is H, alkyl, aryl, cycloalkyl or halogen;

m=1 or 2 and n=0 or 2 wherein the oligomerization temperature ranges between 30° C. and 120° C.

2. The process according to claim 1, wherein R and $R^2$ are H, ($C_1$-$C_{20}$) alkyl, ($C_6$-$C_{20}$)aryl, ($C_3$-$C_{10}$)cycloalkyl, or halogen.

3. The process according to claim 1, wherein $R^2$ is selected from H, $CH_3$, or $C(CH_3)_3$.

4. The process according to claim 1, wherein X is selected from chlorine, β-diketonate, —OR, or —OOCR, wherein R is H, ($C_1$-$C_{20}$) alkyl, ($C_6$-$C_{20}$) aryl, ($C_3$-$C_{10}$) cycloalkyl, or halogen.

5. The process according to claim 1, wherein the zirconium bisphenolate is 2,2'-bissubstituted zirconium(IV) cresolate and/or zirconium(IV)methylene bisphenolate.

6. The process according to claim 1, wherein the co-catalyst is an organo aluminum compound represented by the formula $R^3_p AlY_{3-p}$, wherein $R^3$ is ($C_1$-$C_{20}$) alkyl, Y is halogen and $1 \leq p \leq 2$.

7. The process according to claim 1, wherein the composition comprises an electron donor compound.

8. The process according to claim 1 wherein the oligomerization temperature ranges between 50° C. and 100° C.

* * * * *